(12) United States Patent
Jeong et al.

(10) Patent No.: US 9,538,973 B2
(45) Date of Patent: Jan. 10, 2017

(54) IMAGE RECONSTRUCTION UNIT, X-RAY IMAGING APPARATUS, AND METHOD OF RECONSTRUCTING IMAGE

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Kye Young Jeong, Yongin-si (KR); Jong Ha Lee, Hwaseong-si (KR); Young Hun Sung, Hwaseong-si (KR); Jong Chul Ye, Daejeon (KR); Min Ji Lee, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 45 days.

(21) Appl. No.: 14/550,062

(22) Filed: Nov. 21, 2014

(65) Prior Publication Data
US 2015/0139526 A1 May 21, 2015

(30) Foreign Application Priority Data
Nov. 21, 2013 (KR) .................. 10-2013-0142140

(51) Int. Cl.
*G06T 7/00* (2006.01)
*A61B 6/00* (2006.01)
*G06T 11/00* (2006.01)
*A61B 6/03* (2006.01)

(52) U.S. Cl.
CPC ............. *A61B 6/5217* (2013.01); *A61B 6/032* (2013.01); *A61B 6/037* (2013.01); *A61B 6/5205* (2013.01); *G06T 11/006* (2013.01); *G06T 2211/421* (2013.01)

(58) Field of Classification Search
CPC combination set(s) only.
See application file for complete search history.

(56) References Cited

U.S. PATENT DOCUMENTS 7,251,307 B2 * 7/2007 Chen ................... G06T 11/006 378/21
7,697,658 B2 * 4/2010 Wang .................. G06T 11/006 378/4
8,050,480 B2 * 11/2011 Noo ..................... G06T 11/006 378/4

(Continued)

OTHER PUBLICATIONS

Hengyong Yu, et al., "Compressed sensing based interior tomography" (Abstract), Physics in Medicine and Biology, Published Apr. 15, 2009, total 2 pages, vol. 54, No. 9.

(Continued)

*Primary Examiner* — Anand Bhatnagar
(74) *Attorney, Agent, or Firm* — Sughrue Mion, PLLC

(57) ABSTRACT

An imaging method includes calculating a derivative back projection (DBP) result value using a DBP method with respect to a projection image of a field of view (FOV) inside an object, and reconstructing an image of the FOV by applying a regulation function to the FOV while reconstructing the image of the FOV using the DBP result value.

19 Claims, 13 Drawing Sheets

(56) References Cited

U.S. PATENT DOCUMENTS

| | | | |
|---|---|---|---|
| 8,326,054 B2* | 12/2012 | Chen | A61B 6/032 378/4 |
| 2006/0109952 A1* | 5/2006 | Chen | G06T 11/006 378/4 |
| 2006/0291611 A1* | 12/2006 | Pack | A61B 6/032 378/4 |
| 2008/0049891 A1* | 2/2008 | Yin | G06T 11/006 378/9 |
| 2008/0226016 A1* | 9/2008 | Koehler | G06T 11/006 378/4 |
| 2009/0010518 A1* | 1/2009 | Schoendube | G06T 11/006 382/131 |
| 2009/0196393 A1* | 8/2009 | Wang | G06T 11/006 378/4 |
| 2010/0128958 A1* | 5/2010 | Chen | A61B 6/032 382/132 |
| 2010/0158194 A1* | 6/2010 | Pack | A61B 6/032 378/98.12 |
| 2012/0063659 A1 | 3/2012 | Wang et al. | |
| 2013/0077843 A1 | 3/2013 | Bruder et al. | |

OTHER PUBLICATIONS

M Courdurier, et al., "Solving the interior problem of computed tomography using a priori knowledge" (Abstract), Inverse Problems, Published Sep. 12, 2008, total 3 pages, vol. 24, No. 6.

\* cited by examiner

IMAGE RECONSTRUCTION UNIT, X-RAY IMAGING APPARATUS, AND METHOD OF RECONSTRUCTING IMAGE

CROSS-REFERENCE TO RELATED APPLICATION

This application claims the benefit of Korean Patent Application No. 10-2013-0142140, filed on Nov. 21, 2013 in the Korean Intellectual Property Office, the disclosure of which is incorporated herein by reference in its entirety.

BACKGROUND

1. Field

Exemplary embodiments relate to a method of reconstructing an image and an image reconstruction unit.

2. Description of the Related Art

Imaging apparatuses reconstruct and generate an image based on analog or digital signals converted from various external signals or collected information, and display the image to a user.

Specifically, the imaging apparatus may collect visible rays, infrared rays, X-rays, ultrasonic waves, short waves or microwaves, and the like using a detector, which converts the collected signals into electrical signals and outputs the converted signals. Then, the imaging apparatus may calculate an image corresponding to an ideal image based on the electrical signals output from the detector, i.e., to reconstruct an image.

As the above-described imaging apparatus, for example, a camera, an infrared ray camera, an X-ray imaging apparatus, an ultrasound imaging apparatus, a radar, and the like may be used.

SUMMARY

The exemplary embodiments provide an image reconstruction unit, an X-ray imaging apparatus, and a method of reconstructing an image, which may shorten a time for reconstructing an image with respect to an object based on collected signals, that is, a reconstruction time, and accurately reconstruct the image even when a part of information inside the object is unknown.

The exemplary embodiments also provide an image reconstruction unit, an X-ray imaging apparatus, and a method of reconstructing an image, which may accurately reconstruct an image based on image signals with respect to a partial region inside an object, that is, a field of view (FOV).

In accordance with an aspect of an exemplary embodiment, there is provided a method of reconstructing an image, including: calculating a derivative back projection (DBP) result value using a DBP method with respect to a projection image of a field of view (FOV) inside an object; and reconstructing an image of the FOV by applying a regulation function to the FOV while reconstructing the image of the FOV using the DBP result value.

In accordance with another aspect of an exemplary embodiment, there is provided an image processor including: a derivative back projection (DBP) calculator configured to calculate a DBP result value using a DBP method with respect to a projection image of a field of view (FOV) inside an object; and an image reconstructor configured to reconstruct an image of the FOV inside the object by applying a regulation function to the FOV while reconstructing the image of the FOV using the DBP result value.

In accordance with still another aspect of an exemplary embodiment, there is provided an X-ray imaging apparatus including: an X-ray radiator configured to irradiate a field of view (FOV) inside an object with X-rays; an X-ray detector configured to output electrical signals by converting the X-rays having passed through the FOV; and an image processor configured to acquire a projection image of the FOV inside the object based on the electrical signals, calculate a derivative back projection (DBP) result value using a DBP method with respect to the projection image, and then reconstruct an image of the FOV by applying a regulation function to the FOV while reconstructing the image of the FOV using the DBP result value.

BRIEF DESCRIPTION OF THE DRAWINGS

The above and/or other aspects of the exemplary embodiments will become apparent by describing certain exemplary embodiments, taken in conjunction with the accompanying drawings, in which.

DETAILED DESCRIPTION

Figure 1:
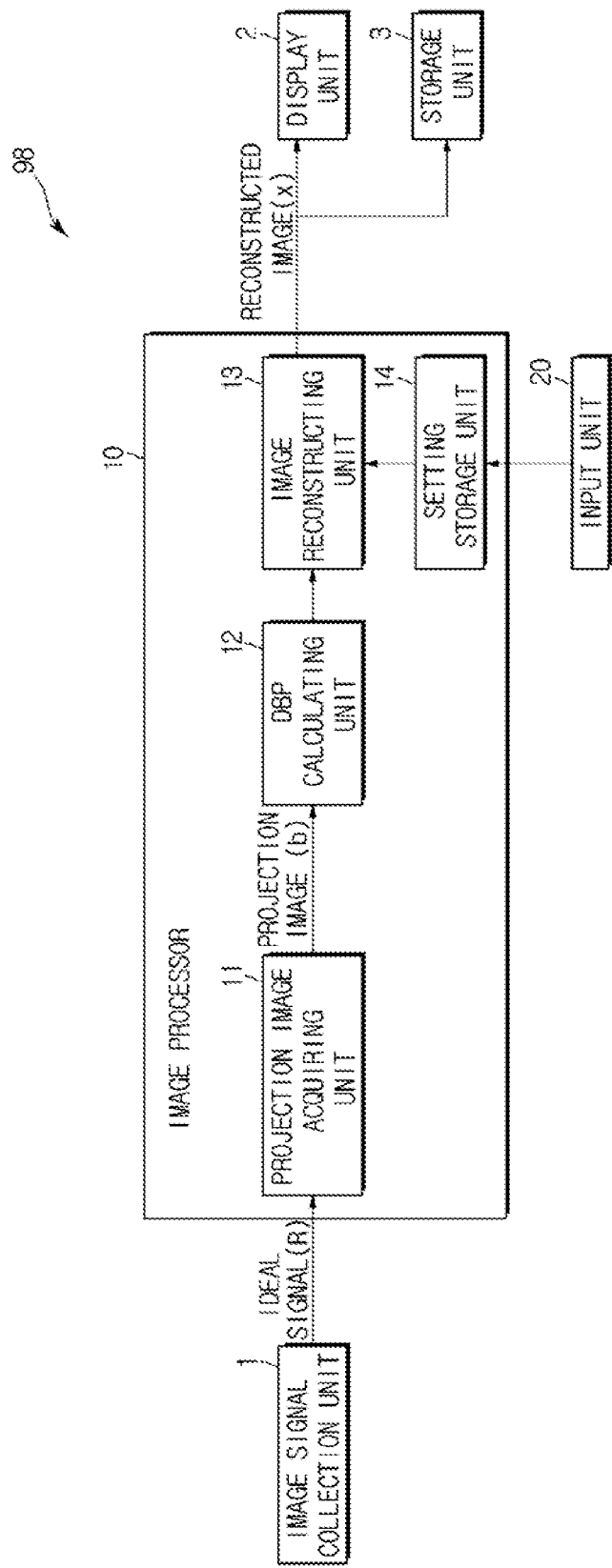
FIG. 1 is a configuration view illustrating an image reconstruction unit in accordance with an exemplary embodiment.

Reference will now be made in detail to certain exemplary embodiments, examples of which are illustrated in the accompanying drawings, wherein like reference numerals refer to like elements throughout.

Hereinafter, an image reconstruction unit in accordance with an exemplary embodiment will be described with reference to FIGS. 1 to 3.

FIG. 1 is a configuration view illustrating an image reconstruction unit in accordance with an exemplary embodiment.

As shown in FIG. 1, an image processor 10 may receive raw data (R) required for image reconstruction from an image signal collection unit 1 (e.g., image signal collector), and enable a reconstructed image (x) corresponding to the raw data (R) to be acquired based on the received raw data (R).

According to an exemplary embodiment, the image signal collection unit 1 may be a detector such as a charged coupled device (CCD) such as an X-ray detection panel of an X-ray imaging apparatus or a camera, and the detector may receive external X-rays or visible rays, convert the received rays into electrical signals, that is, raw data (R), and then output the raw data (R). The output raw data (R) is transmitted to the image processor 10. The raw data (R) collected by the image signal collection unit 1 may be amplified by a predetermined amplification circuit or converted into digital signals by a predetermined analogue-to-digital converter, and then transmitted to the image processor 10, as necessary.

The image processor 10 may transmit the acquired reconstructed image (x) to a display unit 2 (e.g., display), so that a user may view the reconstructed image (x) through the display unit 2. In addition, the image processor 10 may transmit the acquired reconstructed image (x) to a storage unit 3 (e.g., storage) such as a disk storage device or a semiconductor storage device, so that the storage unit 3 may temporarily or non-temporarily store the reconstructed image (x).

The image processor 10 may include a projection image acquiring unit 11 (e.g., projection image acquirer), a derivative back projection (hereinafter, referred to as "DBP") calculating unit 12 (e.g., derivative back projection calculator), and an image reconstructing unit 13 (e.g., image reconstructor) as shown in FIG. 1. In accordance with an exemplary embodiment, the projection image acquiring unit 11, the DBP calculating unit 12, and the image reconstructing unit 13 of the image processor 10 may be implemented by a single processor, and in accordance with another exemplary embodiment, may be implemented by a plurality of processors. For example, each of the projection image acquiring unit 11, the DBP calculating unit 12, and the image reconstructing unit 13 of the image processor 10 may be implemented by a separate processor.

The projection image acquiring unit 11 of the image processor 10 may acquire a projection image (b) of an object using the raw data (R). In this case, the acquired projection image may be a projection image of the entire object, or a projection image of a partial region inside the object, that is, a field of view (FOV). The projection image (b) acquired in the projection image acquiring unit 11 may be transmitted to the DBP calculating unit 12.

The DBP calculating unit 12 may calculate a DBP result value using a derivative back projection (DBP) method with respect to the projection image (b) acquired in the projection image acquiring unit 11. The DBP calculating unit 12 may calculate the DBP result value using the following Equation 1.

$$b(\vec{r_0}) = -\frac{1}{2\pi} \int_{\phi_0}^{\phi_0+\pi} d\phi \left[ \frac{\partial p(s,\phi)}{\partial s} \right]_{s=\vec{r_0}\cdot\vec{u}(\phi)}$$ [Equation 1]

Here, $\vec{r_0}$ denotes a reconstructing point vector on a two-dimensional) space, and $b(\vec{r_o})$ denotes a DBP result value with respect to the reconstructing point vector $\vec{r_0}$ on the two-dimensional space. $p(s,\phi)$ denotes a projection image signal with respect to the projection image (b). Meanwhile, s denotes a distance of the projection ray from an origin, and φ denotes an angle of the projection ray. Here, $\phi_0$ may be obtained as an arbitrary angle. In addition, u(φ) may be obtained as shown in the following Equation 2:

$$\vec{u}(\phi) = (\cos \phi, \sin \phi)$$ [Equation 2]

When calculating the DBP result value with respect to the projection image in the DBP calculating unit 12 using Equation 2, the calculated DBP result value may be transmitted to the image reconstructing unit 13.

The image reconstructing unit 13 may reconstruct an image of the object using the DBP result value calculated in the DBP calculating unit 12. More specifically, the image reconstructing unit 13 may calculate an internal luminance value of the object using the DBP result value to reconstruct an image of the inside of the object.

In accordance with an exemplary embodiment, the image reconstructing unit 13 may reconstruct an image of an FOV inside the object rather than the entire object.

Figure 2A:
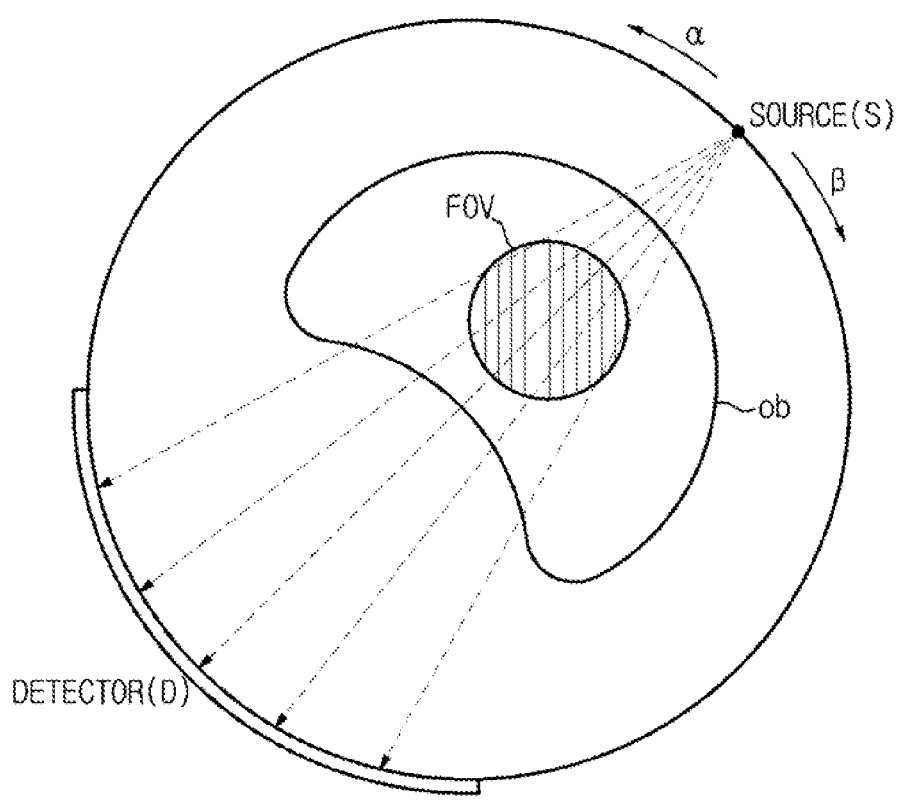
FIG. 2A illustrates X-ray irradiation on a part of an object in accordance with an exemplary embodiment.
Figure 2B:
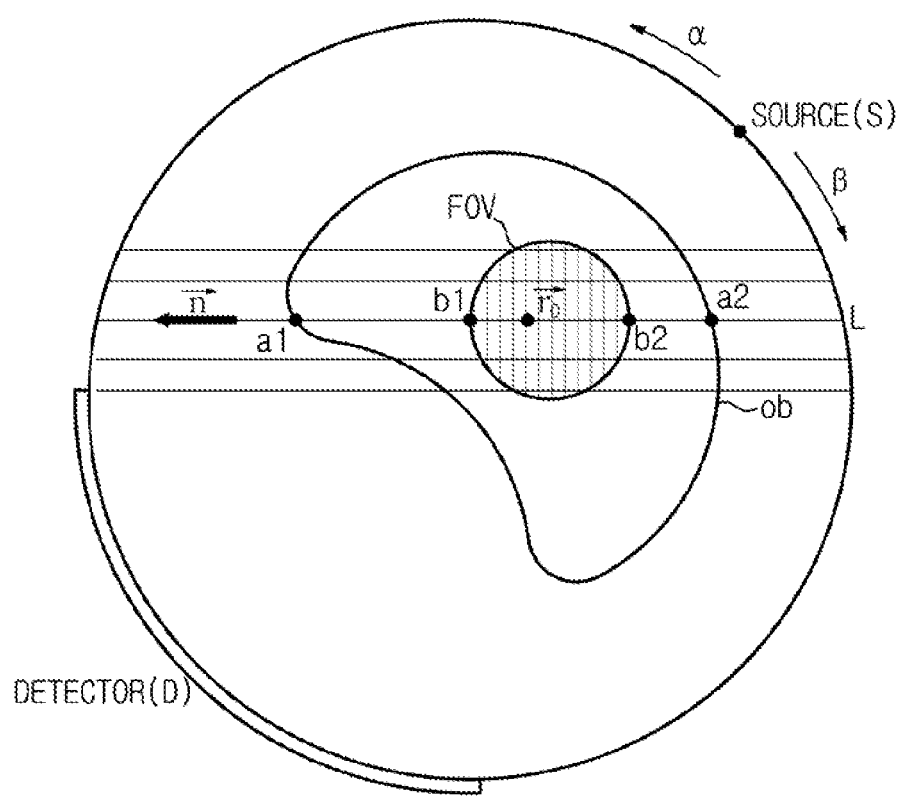
FIG. 2B illustrates a circular source trajectory and chord line when X-ray irradiation is performed on a part of a 2D object in accordance with an exemplary embodiment.

FIG. 2A illustrates X-ray irradiation on a part of an object in accordance with an exemplary embodiment and FIG. 2B illustrates a circular source trajectory and chord line when X-ray irradiation is performed on a part of a 2D object in accordance with an exemplary embodiment.

The image reconstructing unit 13 may be used to reconstruct an X-ray image in an X-ray imaging apparatus in accordance with an exemplary embodiment. As shown in FIG. 2A, X-rays may be irradiated from a predetermined X-ray source (s), and the X-rays transmitted through an object (ob) may be detected by a predetermined detector (d). The X-ray source (s) may be moved in a predetermined direction (α or β direction), and consequently, rotationally moved around the object (ob). In this case, the detector (d) may be symmetrically moved along the movement of the X-ray source (s) in the same manner as in the X-ray source (s) so that the X-rays irradiated from the X-ray source (s) are appropriately received.

In case of imaging the X-rays, there are technical problems such as a case in which a size of the object (ob) is relatively large or a size of the detector (d) is relatively smaller than the object (ob), and therefore only a part of the object (ob) may be imaged. In addition, at the time of diagnosis or the like, there may be a case in which only an image of a part of the inside of the object (ob) is required. In this case, the X-ray source (s) may be irradiated only to the FOV of a part of the inside of the object (ob), and the detector (d) may detect only the X-rays transmitted through only the FOV of the inside of the object (ob), so that X-rays transmitted through only the FOV of the inside of the object (ob) may be converted into electrical signals to be output.

The image reconstructing unit 13 may reconstruct an X-ray image of the FOV inside the object (ob) based on the electrical signals to which the X-rays transmitted through only the FOV of the inside of the object (ob) in this manner are converted. According to an exemplary embodiment, the electrical signals may be raw data output from the detector (d), or signals acquired by amplifying the raw data or performing a predetermined conversion such as analogue-to-digital conversion on the raw data.

The image reconstructing unit 13 may reconstruct the image of the FOV inside the object (ob) using a predetermined regulation function. According to an exemplary embodiment, the applied predetermined regulation function may be, for example, total variation (TV). Such a regulation function may be defined in advance by a user or determined in accordance with a setting of the system. In accordance with an exemplary embodiment, the image reconstructing unit 13 may reconstruct the image by applying a predetermined regulation function to the FOV inside the object (ob). This will be described later.

In addition, the image reconstructing unit 13 may reconstruct the image of the FOV inside the object using information about the outline of the object (curved line passing through a1 and a2 in FIG. 2B) together with the regulation function.

The image reconstructing unit 13 may reconstruct the image of the FOV inside the object (ob) using at least one condition or at least one cost function. Specifically, the image reconstructing unit 13 may acquire a value for satisfying the at least one condition (may include a predetermined function) or acquire a value for minimizing or maximizing the cost function to thereby acquire an internal luminance value. The image may be reconstructed based on the acquired internal luminance value. The at least one condition or the at least one cost function may be selected or set by a user, or defined in advance by the system.

Meanwhile, in accordance with an exemplary embodiment, the image reconstructing unit 13 may reconstruct the image of the FOV using a projection onto convex set (POCS) method. In addition, in accordance with another exemplary embodiment, the image reconstructing unit 13 may reconstruct the image of the FOV inside the object using a parallel proximal algorithm (PPXA).

Hereinafter, an example in which the image reconstructing unit 13 uses the POCS method will be described.

When an internal luminance value of an object is $\mu(\vec{r})$, a DBP result value $b(\vec{r_0})$ that can be calculated by Equation 1 may have a relationship with the internal luminance value $\mu(\vec{r})$ of the object as shown in the following Equation 3:

$$b(\vec{r_0}) = \frac{1}{\pi} P \cdot V \cdot \int_{-\infty}^{\infty} \frac{dt}{t} \mu(\vec{r_0} - \vec{m}) = (H_L \mu)(\vec{r_0}) \quad \text{[Equation 3]}$$

Here, H denotes one-dimensional Hilbert transform in a direction L, and L denotes a straight line that passes through $\vec{r_0}$ and is parallel with $\vec{n}$. P.V. may be a Cauchy principal value as a principle value.

According to an exemplary embodiment, Equation 3 may be used even when only a value on the straight line L of the entire two dimensions $b(\vec{r_0})$ and $\mu(\vec{r})$ is known, and therefore a calculation is performed by changing a two-dimensional problem to a one-dimensional problem. That is, as shown in FIG. 2B, the FOV inside the object (ob) is divided into one-dimensional horizontal line segments like the straight line connected to two points on a source trajectory to be calculated. In this case, the one-dimensional line segment may be met with the outline of the object (ob) at points $a_1$ and $a_2$ shown in FIG. 2B, and met with the FOV at points $b_1$ and $b_2$.

When Equation 3 is made into one dimension to be simplified, the following Equation 4 is obtained:

$$g(x) = \frac{1}{\pi} P \cdot V \cdot \int_{-\infty}^{\infty} dx' \frac{1}{x-x'} f(x') = (Hf)(x) \quad \text{[Equation 4]}$$

Here, g(x) denotes a one-dimensional DBP result value, and f(x) denotes a one-dimensional internal luminance value. x denotes a position value with respect to a point where the luminance value is restored. That is, x denotes a value indicating each point existing on any one line segment connecting two points on a source trajectory shown in FIG. 2B. In the same manner as in Equation 3, a one-dimensional DBP result value of Equation 4 also has a relationship between the one-dimensional internal luminance value and Hilbert-transforming.

In this manner, using the relationship between the one-dimensional DBP result value and the one-dimensional internal luminance value, the image reconstructing unit 13 may set at least one condition with respect to the internal luminance value in advance, select at least one value corresponding to the at least one condition set in advance to acquire an internal luminance value, and then reconstruct a predetermined image using the acquired internal luminance value.

In this case, the image reconstructing unit 13 may reconstruct the image by acquiring the internal luminance value using an iterative reconstruction method. For example, the image reconstructing unit 13 may acquire an optimal internal luminance value by repetitively substituting a predetermined value for each of the at least one condition in accordance with a predetermined order, and then reconstruct the image based on the acquired optimal internal luminance value.

In accordance with an exemplary embodiment, the at least one condition with respect to the internal luminance value used by the image reconstructing unit 13 may differ depending on a point to be reconstructed.

For example, when the point to be reconstructed exists inside the FOV, that is, when the point to be reconstructed exists between the points $b_1$ and $b_2$ in FIG. 2B, a condition in which a difference between a one-dimensional DBP result value g(x) and a Hilbert-transforming result value of a one-dimensional internal luminance value f(x) should be minimized may be given (first condition).

When the point to be reconstructed exists outside the object (ob), that is, when the point to be reconstructed does not exist between the points $a_1$ and $a_2$ of FIG. 2B, the internal luminance value f(x) should be zero. This is because the outside of the object (ob) is an area in which radiation is not attenuated and the internal luminance value cannot be acquired (second condition). Here, the points $a_1$ and $a_2$ are values where the outline of the object (ob) is positioned. Thus, the second condition may indicate that information about the outline of the object (ob) is known. The outline of the object (ob) is exposed to the outside, and therefore it can be sufficiently seen using various measurement methods.

Since the inside of the object (ob) is the area in which radiation is attenuated, the internal luminance value f(x) should be larger than 0 when the point to be reconstructed exists inside the object (ob), that is, when the point to be reconstructed exists between the points $a_1$ and $a_2$ of FIG. 2B (third condition).

When the point to be reconstructed exists inside the FOV of the object (ob), that is, when the point to be reconstructed exists between $b_1$ and $b_2$ of FIG. 2B, the internal luminance value f(x) may be defined as a regulation function (fourth condition). According to an exemplary embodiment, the regulation function may be acquired in accordance with total variation (TV). In this manner, when the point to be reconstructed exists inside the FOV of the object (ob), the condition is defined using the regulation function, and therefore the internal luminance value f(x) may be acquired even without acquiring an internal luminance value in advance inside the FOV. Thus, it is not necessary to know an internal luminance value of a part of the inside of the FOV which is practically difficult to understand. Meanwhile, the line integral of the internal luminance value f(x) should be acquired from projection image signals (fifth condition).

The above-described five conditions are represented as the following Equations 5 to 9:

$$C_1 = \{\tilde{f} \in L^2(R) \| |(H\tilde{f})(x) - g^\varepsilon(x)| \le \varepsilon, x \in [b_1, b_2]\} \quad \text{[Equation 5]}$$

$$C_2 = \{\tilde{f} \in L^2(R) | \tilde{f}(x) = 0, x \notin [a_1, a_2]\} \quad \text{[Equation 6]}$$

$$C_3 = \{\tilde{f} \in L^2(R) | \tilde{f}(x) \ge 0, x \in [a_1, a_2]\} \quad \text{[Equation 7]}$$

$$C_4 = \{\tilde{f} \in L^2(R) | \min_{\tilde{f}(x,y)} = TV(\tilde{f}(x,y)), x \in [b_1, b_2]\} \quad \text{[Equation 8]}$$

$$C_5 = \left\{ \tilde{f} \in L^2(R) \left| \frac{1}{\pi} \int_{a_1}^{a_2} dx \tilde{f}(x) = C_f = \frac{1}{\pi} p(\vec{u}(\phi_o) \cdot \vec{r_0}, \phi_0) \right. \right\} \quad \text{[Equation 9]}$$

Here, $\tilde{f}(x)$ may denote a function f(x) indicating a two-dimensional internal luminance value or another function similar to a function (f).

Equation 8 is obtained by using TV as a regulation function. Equation 8 is obtained by applying internal luminance total variation (TV) to two-dimensional projection image signals unlike Equations 6, 7, and 9. Thus, a y value as well as an x value is expressed in Equation 8. For example, total variation (TV) may be applied to one-dimensional image signals. When total variation (TV) is applied to the two-dimensional signals, quality of the image may be improved. Meanwhile, a regulation function that can be used in Equation 8 is not limited to total variation (TV), and other regulation functions may be equally used.

The image reconstructing unit 13 may enable the condition to differ depending on a point in which each luminance value is reconstructed, and acquire at least one optimal internal luminance value f(x) that meets all of the different conditions to reconstruct an image.

The image reconstructing unit 13 may detect the at least one optimal internal luminance value f(x) sequentially using the above-described conditions in accordance with an exemplary embodiment. That is, the image reconstructing unit 13 may project a predetermined value to the above-described condition in accordance with a predetermined order. For example, the image reconstructing unit 13 may acquire the internal luminance value f(x) by projecting a predetermined value to the second condition, the first condition, the fourth condition, the fifth condition, and the third condition in the stated order. For example, the order to project the predetermined value to the above-described conditions is not limited thereto. Further, it is possible to project the predetermined value to the above-described conditions in accordance with various orders. In addition, the predetermined value may be simultaneously projected to the above-described first to fifth conditions.

Hereinafter, an example in which the image reconstructing unit 13 uses a PPXA will be described.

The PPXA is a method in which at least one cost function is determined in the same manner as in the at least one condition of the POCS method and at least one optimal internal luminance value f(x) is detected by detecting a value for minimizing a sum of the determined at least one cost function. According to the PPXA, a final result may be the same as that of the POCS method. However, when using the PPXA, the internal luminance value f(x) may be more quickly acquired compared to the POCS method. This is because the POCS method sequentially calculates each condition, whereas the PPXA calculates each cost function in parallel.

According to the example using the PPXA, the image reconstructing unit 13 may acquire the at least one optimal internal luminance value f(x) by using the following Equation 10:

$$\hat{f} = \underset{f \in R^N}{\operatorname{argmin}} \sum_{j=1}^{J} \psi_j(\tilde{f}) \quad \text{[Equation 10]}$$

Here, $\psi_j(\cdot)$ denotes a cost function, and j denotes an identification number for identifying each cost function. J denotes a total number of the cost functions. That is, by detecting f for minimizing a sum of each of the cost functions, the at least one optimal internal luminance value f(x) may be acquired. Clearly, in accordance with exemplary embodiments, by detecting f for satisfying a minimum value of a sum of absolute values of the cost function or a minimum value of a sum of squares of the cost function, at least one optimal internal luminance value f(x) may be acquired.

According to an exemplary embodiment, the cost function $\psi_j$ may be obtained by using the following Equations 11 to 14:

$$\psi_1(\tilde{f}) = \quad \text{[Equation 11]}$$
$$c_1(\tilde{f}(x)) = \begin{cases} 0 & \text{if } |(H\tilde{f})(x) - g^\varepsilon(x)| \le \varepsilon, x \in [b_1, b_2] \\ +\infty & \text{otherwise} \end{cases}$$

$$\psi_2(\tilde{f}) = c_2(\tilde{f}(x)) = \begin{cases} 0 & \text{if } \tilde{f}(x) = 0, x \notin [a_1, a_2] \\ +\infty & \text{otherwise} \end{cases} \quad \text{[Equation 12]}$$

$$\psi_3(\tilde{f}) = c_3(\tilde{f}(x)) = \begin{cases} 0 & \text{if } \tilde{f}(x) \ge 0, x \in [a_1, a_2] \\ +\infty & \text{otherwise} \end{cases} \quad \text{[Equation 13]}$$

$$\psi_4(\tilde{f}) = c_4(\tilde{f}(x,y)) = TV(f, (x, y)), x \in [b_1, b_2] \quad \text{[Equation 14]}$$

In Equation 11, a first cost function indicates that a difference between the DBP result value g(x) and the internal luminance value f(x) should be minimized, and in Equation 12, a second cost function indicates that the internal luminance value f(x) is zero when the point to be reconstructed exists outside the object (ob). In Equation 13, a third cost function indicates that the internal luminance value f(x) should be greater than zero inside the object (ob).

In Equation 14, a fourth cost function indicates that the internal luminance value f(x) may be defined as a regulation function when the point to be reconstructed exists in any one point inside the FOV of the object (ob). That is, a cost function with respect to a part of the FOV inside the object (ob) may be acquired based on the regulation function.

The fourth cost function corresponds to an example in which total variation (TV) is used as the regulation function. The total variation (TV) may be acquired by applying the technique to one-dimensional projection image signals, or may be acquired by applying to two-dimensional projection image signals, by using Equation 14. When the cost function is calculated using the two-dimensional projection image signals in Equation 14, the calculation is performed using the entire chord line. Meanwhile, the regulation function that can be used in the fourth cost function is not limited to the total variation (TV), and other regulation functions may be also used.

As to the first to fourth cost functions, when a substituted value (function) corresponds to a condition after an if statement of the right side, each cost function has a value of zero, and when the substituted value does not correspond to the condition after the if statement, the cost function has an infinite value. Thus, a minimum value of a sum (Equation 10) of the cost functions is obtained in the same manner as in detecting a value $\tilde{f}(x)$ that meets all of the conditions after the if statement of the right side. Thus, consequently, the same result as a result obtained when calculation is performed using Equations 5 to 9 may be obtained.

The image reconstructing unit 13 may acquire at least one optimal internal luminance value f(x) in accordance with the PPXA using the above-described Equations 11 to 14. The image reconstructing unit 13 may also use an iterative reconstruction method even when using the PPXA.

The image reconstructing unit 13 may apply a different cost function depending on a reconstructed position like Equations 11 to 14, acquire a minimum value of a sum of the cost functions to acquire the at least one optimal internal luminance value f(x), and reconstruct an image using the acquired at least one optimal internal luminance value f(x).

As described above, the example in which the fan-beam X-ray source (s) and/or the 1D detector (d) is moved in a predetermined direction or rotationally moved around the object (ob) has been described with reference to FIG. 2B. As shown in FIG. 2B, a two-dimensional image like a cross-sectional area of the object (ob) may be reconstructed. The above description will be equally applied even when reconstructing a three-dimensional image.

Figure 3:
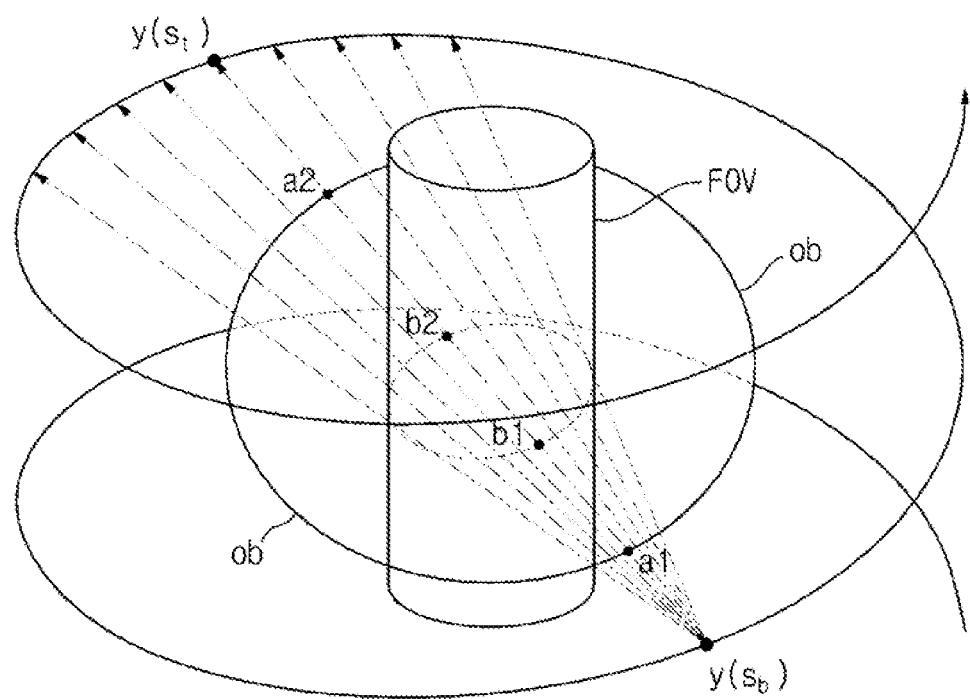
FIG. 3 illustrates a helical source trajectory and PI lines when X-ray irradiation is performed on a part of a 3D object in accordance with another exemplary embodiment.

FIG. 3 illustrates a helical source trajectory and PI lines when X-ray irradiation is performed on a part of a 3D object in accordance with another exemplary embodiment.

In FIG. 3, an example of PI lines of $y(s_b)$ and $y(s_t)$ to cover the FOV while rotating along a helical trajectory around the object (ob) is illustrated. When the $y(s_b)$ and the $y(s_t)$ are helically moved, an FOV may have a cylindrical shape as shown in FIG. 3.

As shown in FIG. 3, a three-dimensional space that desires to return to a set of PI lines is illustrated, and therefore a three-dimensional image may be reconstructed. The PI line denotes a line connecting two points $y(s_b)$ and $y(s_t)$ within 360 degrees on a helical trajectory, and has the same function as the above-described chord line. Thus, when the projection image acquiring unit 11 acquires a projection image and the DBP calculating unit performs a DBP process, the image reconstructing unit 13 may reconstruct a three-dimensional image in the same manner as or a similar manner to that described with respect to FIG. 2B. In this case, the image reconstructing unit 13 may acquire at least one optimal internal luminance value using the above-described POCS method or the PPXA.

Hereinafter, a method of reconstructing a three-dimensional image will be described in detail. A helical trajectory $\vec{y}(s)$ on three dimensions may be represented as the following Equation 15:

$$\vec{y}(s) = \left( R\cos(s), R\sin(s), \frac{h}{2\pi}s \right) \quad \text{[Equation 15]}$$

Here, h denotes a helical pitch, and R denotes a helical radius. Here, a projection image may be represented as the following Equation 16:

$$p(\vec{y}, \vec{\beta}) = \int_0^\infty f(\vec{y} + \vec{\beta}t)dt, \quad \vec{\beta} \in S^2 \quad \text{[Equation 16]}$$

Here, $f(\tilde{x})$ denotes an attenuation coefficient function on a three-dimensional space, and $S^2$ denotes a unit space. $\beta$ denotes an arbitrary constant belonging to a unit space. When a DBP method is applied, a DBP result value of $p(\vec{y}, \vec{\beta})$ may be represented as the following Equation 17:

$$g(\vec{x}) = \frac{-1}{2\pi} \int_{s_b}^{s_t} \frac{ds}{|\vec{x} - \vec{y}(s)|} \left[ \frac{\partial}{\partial q} p(\vec{y}(q), \vec{\beta}(s, \vec{x})) \right]_{q=s} \quad \text{[Equation 17]}$$

Here, $g(\vec{x})$ denotes a DBP result value of $p(\vec{y}, \vec{\beta})$, and $s_b$ and $s_t$ respectively denote a start point and an end point of the PI line of the helical trajectory. $\vec{\beta}(s, \vec{x})$ denotes a projection direction vector.

When the DBP result value on each PI line is calculated, back-projection may be performed based on projection of PI-segment, which is the same as or substantially the same as a process of acquiring the DBP result value of a projection vector on the above-described two-dimensional space. Thus, based on this relationship, when calculating the DBP result value of the projection vector on the three-dimensional space, the above-described Equation 17 may be obtained.

In this manner, when acquiring the DBP result value along the PI line, the image reconstructing unit 13 may reconstruct a three-dimensional image using the same method as or a similar method to that described with respect to FIG. 2A and FIG. 2B considering the PI line as the chord line.

As shown in FIG. 1, the image processor 10 may further include a setting storage unit 14 (e.g., setting storage). The setting storage unit 14 may store a variety of settings required for image reconstruction. For example, the setting storage unit 14 may store various settings selected through an input unit 20 by a user or input by the user, and transmit the stored setting to the image reconstructing unit 13, and therefore the image reconstructing unit 13 may reconstruct an image in accordance with the user's selection. For example, when the user selects any one of the above-described POCS method or PPXA through the input unit 20, the input unit 20 may output predetermined electrical signals in accordance with the user's selection to transmit the output electrical signals to the setting storage unit 14, and the setting storage unit 14 may transmit the stored setting to the image reconstructing unit 13, and therefore an image may be reconstructed in accordance with any one of the POCS method and the PPXA.

In accordance with an exemplary embodiment, the setting storage unit 14 may store the above-described first to fifth conditions or first to fourth cost functions. When reconstructing the image using the above-described first to fifth conditions or the first to fourth cost functions, by the image reconstructing unit 13, the setting storage unit 14 may transmit the stored first to fifth conditions or first to fourth cost functions to the image reconstructing unit 13 in accordance with call signals generated in the image reconstructing unit 13.

Hereinafter, a method of reconstructing an image will be described with reference to FIG. 4.

The image (x) reconstructed by the image processor 10 is transmitted to the display unit 2 or storage unit 3. The display unit 2 displays the reconstructed image (x) to a user. The display unit 2 may be various types of display devices. The storage unit 3 may temporarily or non-temporarily store the reconstructed image (x). The storage unit 3 may be a magnetic disk storage device or a semiconductor storage device.

Hereinafter, a method of reconstructing an image in accordance with an exemplary embodiment will be described.

Figure 4:
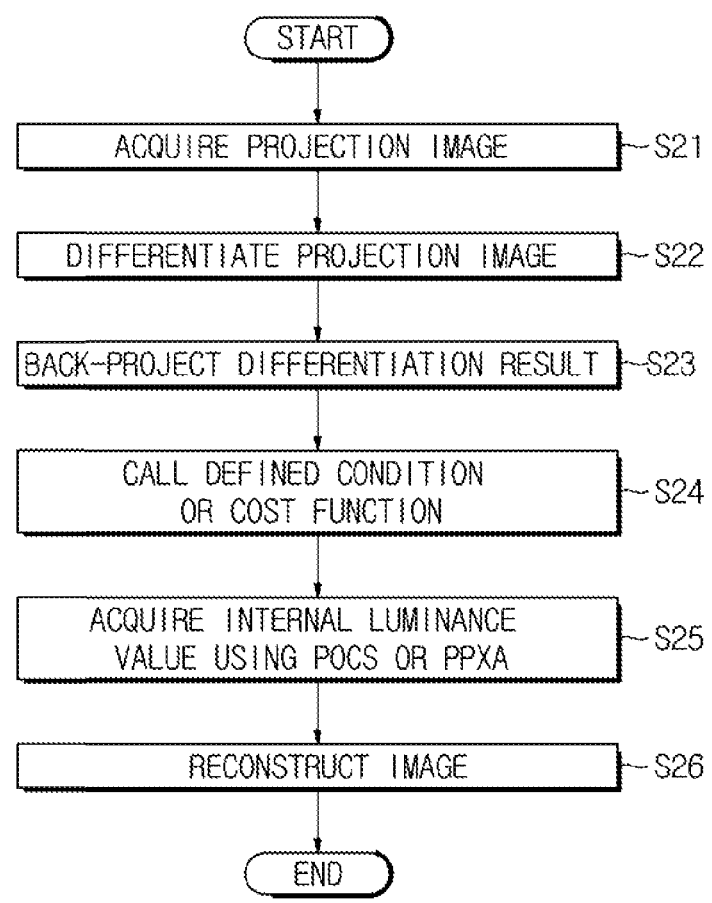
FIG. 4 is a flowchart illustrating a method of reconstructing an image in accordance with an exemplary embodiment.

FIG. 4 is a flowchart illustrating a method of reconstructing an image in accordance with an exemplary embodiment.

As shown in FIG. 4, in operation S21, the method in accordance with an exemplary embodiment acquires a predetermined projection image with respect to an object. Here, the acquired predetermined projection image may be a projection image of the entire object, or a projection image of a partial region inside the object, that is, a field of view (FOV).

Next, the method differentiates the acquired projection image (b) in operation S22, and back-projects a result of the differentiation to obtain a DBP result value in operation S23. In this instance, the DBP result value may be calculated using Equation 1 or Equation 17 which has been described above.

When the DBP result value is acquired, the method may reconstruct an image with respect to the inside of the object using the DBP result value. In this case, the acquired image may be an image of the FOV inside the object. More specifically, a predetermined condition or a cost function may be first called in accordance with a system setting or a user's selection in operation S24. Here, the called predetermined conditions may be the first to fifth conditions, and the first to fifth conditions may be given in accordance with, for example, Equations 5 to 9. In addition, the called cost functions may be the first to fourth cost functions, and the first to fourth cost functions may be given in accordance with Equations 11 to 14. When the cost function is called, a value that satisfies a minimum value of a sum of the first to fourth cost functions may be recognized as at least one optimal internal luminance value.

When the predetermined condition or the cost function is called, the POCS method or the PPXA may be performed in operation S25. When reconstructing an image using the POCS method, the above-described first to fifth conditions may be used in the image reconstruction. When reconstructing the image using the PPXA, the first to fourth cost functions may be used in the reconstruction. The POCS method or the PPXA may be performed by an iterative reconstruction method.

In operation S26, based on a result obtained by performing the POCS method or the PPXA, an image of the object may be reconstructed.

Hereinafter, with reference to FIGS. 5 to 11, an example of a digital radiography (DR) imaging apparatus and a computed tomography (CT) imaging apparatus to which the image reconstruction unit according to an exemplary embodiment is applied will be described.

An X-ray imaging apparatus is an imaging apparatus for acquiring X-ray images of materials inside an object or a structure or tissue of the object using mutually different radiation attenuation rates among the materials inside the object, and may easily understand an internal structure of the object without destructing the object.

Specifically, the X-ray imaging apparatus may irradiate the object with X-rays, collect the X-rays transmitted through the object, and then reconstruct an image using the collected X-rays, thereby acquiring an image inside the object. Here, the object may be a human body or an article such as luggage.

As an example of the X-ray imaging apparatus, a DR imaging apparatus, a CT imaging apparatus, a mammography imaging apparatus, a fluoroscopy imaging apparatus, a cardiac imaging apparatus, or the like may be used. For the convenience of description, the DR imaging apparatus and the CT imaging apparatus of the X-ray imaging apparatus to which the image processing unit is applied have been described, but the X-ray imaging apparatus to which the image processing unit may be applied is not limited thereto.

Figure 5:
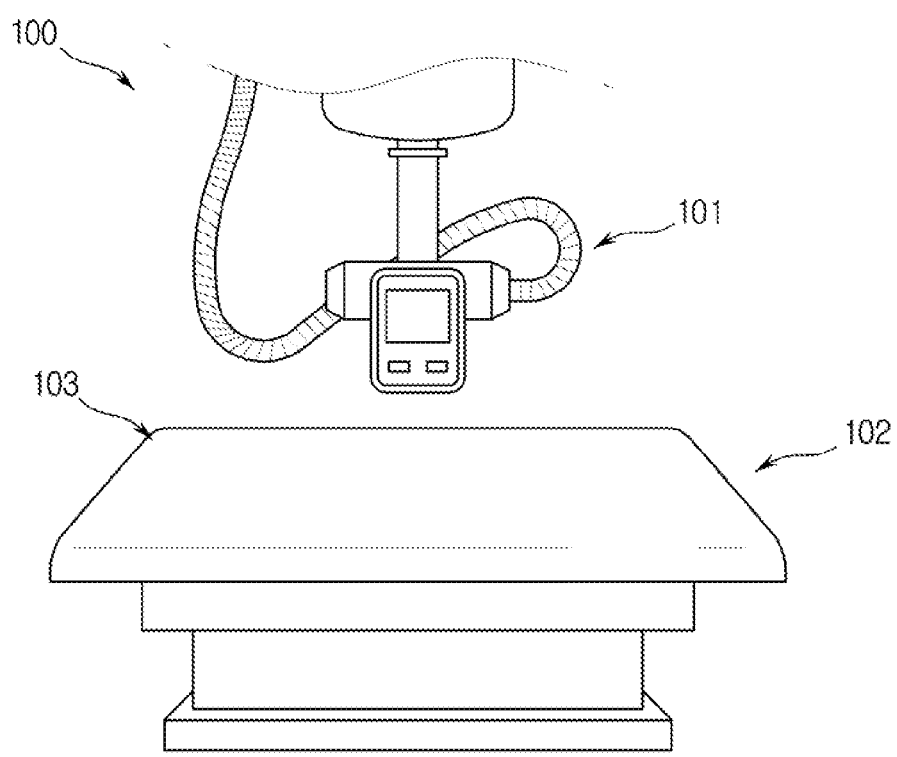
FIG. 5 is a front view illustrating an X-ray imaging apparatus in accordance with an exemplary embodiment.
Figure 6:
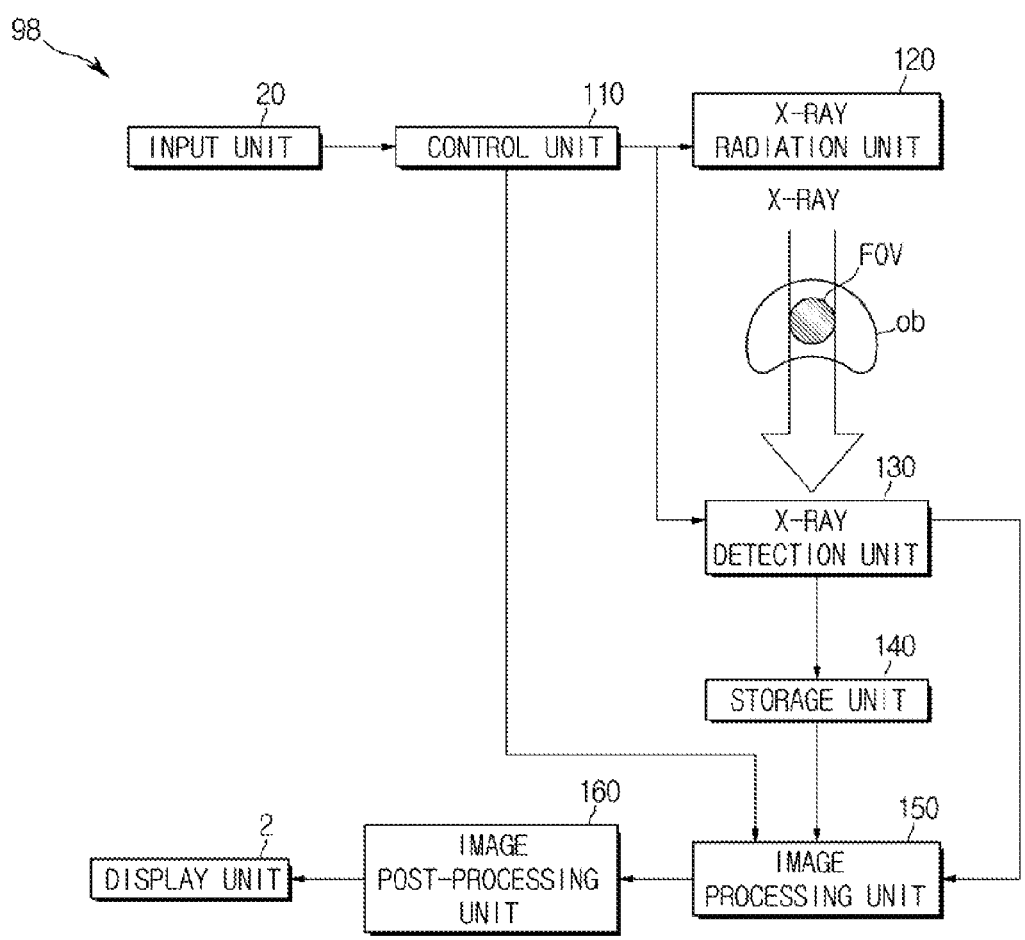
FIG. 6 is a configuration view illustrating an X-ray imaging apparatus in accordance with an exemplary embodiment.

FIG. 5 is a front view illustrating a DR imaging apparatus of the X-ray imaging apparatus 98 in accordance with an exemplary embodiment, and FIG. 6 is a configuration view illustrating an X-ray imaging apparatus in accordance with an exemplary embodiment.

Hereinafter, as an example of an X-ray imaging apparatus 98, a DR imaging apparatus 100 will be described.

As shown in FIGS. 5 and 6, the DR imaging apparatus 100 may include an X-ray radiation module 101 in which an X-ray radiation unit 120 (e.g., X-ray radiator) that generates X-rays and then irradiates an object (ob) with the X-rays is provided. The X-ray radiation module 101 may irradiate the object with the X-rays in a predetermined direction, that is, in a ground surface direction as shown in FIG. 5. Of course, the X-ray radiation module 101 may irradiate the object with the X-rays in other directions, such as in a horizontal direction parallel to the ground.

The X-ray imaging apparatus 98 may include an X-ray detection module 102 including an X-ray detection unit 130 that receives the X-rays transmitted through the object (ob). As shown in FIG. 5, a holding unit 103 (e.g., holder) in which an object to be irradiated with X-rays is placed may be formed in one side of the X-ray detection module 102, and the X-ray detection unit 130 (e.g., X-ray detector) of the X-ray detection module 102 may be mounted in a lower portion of the holding unit 103. The holding unit 103 may be made of a material through which X-rays can be transmitted.

As shown in FIG. 6, the X-ray imaging apparatus 98 in accordance with an exemplary embodiment may include an input unit 20 (e.g., inputter), the X-ray radiation unit 120, the X-ray detection unit 130, a storage unit 140 (e.g., storage), an image processing unit 150 (e.g., image processor), an image post-processing unit 160 (e.g., image post-processor), and a display unit 2 (e.g., display).

The input unit 20 may receive various instructions or commands concerning X-ray imaging or X-ray image processing from a user or the like, and generate predetermined signals in accordance with the various instructions or commands to transmit the generated signals to a control unit 110, e.g., a controller. In accordance with an exemplary embodiment, the input unit 20 may be a user interface that is directly mounted in the X-ray imaging apparatus 98, or mounted in or connected to a separate workstation. Here, the workstation may transmit and receive data with the X-ray imaging apparatus 98 through a wired or wireless communication network. The input unit 20 may include various buttons, a keyboard, a mouse, a track-ball, a track-pad, a touchscreen panel, various levers, a handle, a stick, or the like.

The control unit 110 may generate a predetermined control command, and transmit the generated control command to the X-ray radiation unit 120, the X-ray detection unit 130, the storage unit 140, or the image processing unit 150, thereby controlling general operations of the X-ray imaging apparatus 98. The control unit 110 may control predetermined operations of the X-ray imaging apparatus 98 in accordance with electrical signals caused by instructions or commands of the user input from the input unit 20, or in accordance with a setting determined in advance.

For example, the control unit 110 may generate predetermined control signals and transmit the generated control signals to the X-ray radiation unit 120, and the X-ray radiation unit 120 may apply power of a predetermined voltage to an X-ray tube in accordance with the control signals of the control unit 110 to generate X-rays of predetermined energy. In addition, the control unit 110 may also control a movement operation of the X-ray radiation unit 120. The X-ray radiation unit 120 may be linearly or rotationally moved around the object (ob) in accordance with control of the control unit 110.

The control unit 110 may control various operations of the X-ray detection unit 130 such as movement of the X-ray detection unit 130, reading of the received X-ray signals, and the like. For example, the control unit 110 may generate a control command for moving the X-ray detection unit 130 so that the X-rays can be appropriately received in accordance with the movement of the X-ray radiation unit 120. In addition, the control unit 110 may control the X-ray signals stored in the X-ray detection unit 130 to be transmitted to the storage unit 140, and therefore the storage unit 140 may temporarily or non-temporarily store the X-ray signals.

In addition, the control unit 110 may control operations of a collimator or various filters, as necessary.

The control unit 110 may include various processors including at least one chip in which an integrated circuit is formed, and such a central processing unit may be provided inside the X-ray imaging apparatus 98 or in a separate workstation.

The X-ray radiation unit 120 may irradiate the object (ob) with X-rays of predetermined energy. In accordance with an exemplary embodiment, the X-ray radiation unit 120 may irradiate the entire object (ob) with X-rays, or as shown in FIG. 6, irradiate only a specific region inside the object (ob), that is, the FOV with the X-rays.

Figure 7:
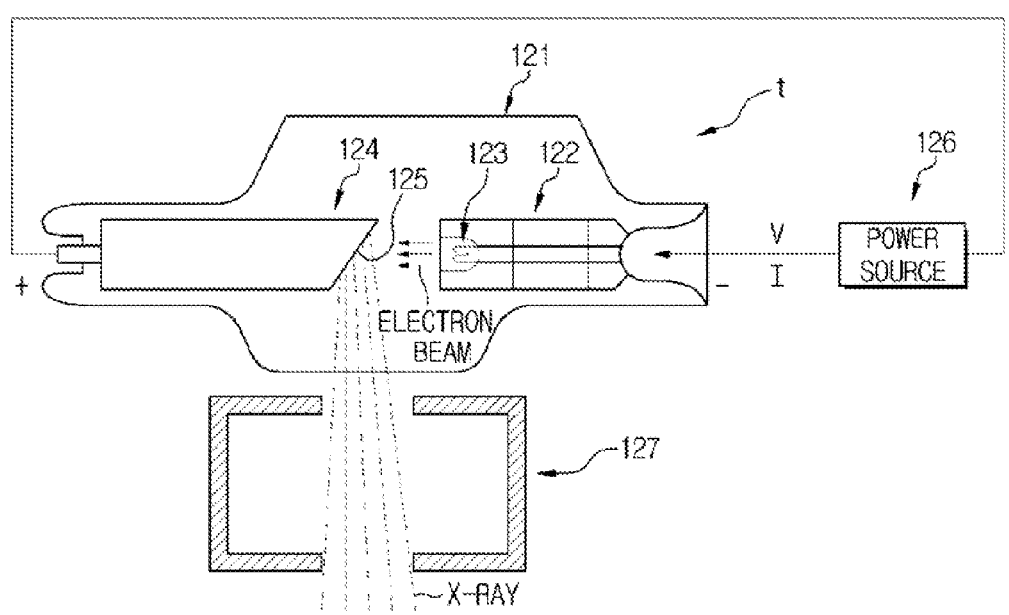
FIG. 7 is a conceptual view illustrating an X-ray irradiation unit in accordance with an exemplary embodiment.

FIG. 7 is a conceptual view illustrating an X-ray irradiation unit in accordance with an exemplary embodiment.

As shown in FIG. 7, the X-ray radiation unit 120 may include an X-ray tube (t) for generating X-rays and a power source 126 for applying a voltage to the X-ray tube (t).

The X-ray tube (t) may include a pipe body 121 including other various parts, a cathode 122, and an anode 124.

The pipe body 121 may maintain a vacuum level within the pipe body 121 at about $10^{-7}$ mmHg while stably fixing the cathode 122 and the anode 124 within the pipe body 121. The pipe body 121 may be a glass pipe made of a rigid silicate glass.

A filament 123 in which a plurality of electrons gather may be formed in the cathode 122. A carbon nanotube may be formed in the cathode 122 instead of the filament 123. In addition, the cathode 122 may include a focusing electrode for focusing emitted electrons, as necessary.

The filament 123 may be electrically connected to the power source 126 to be heated in accordance with a tube voltage applied from the power source 126. When the filament 123 is heated, the plurality of electrons which gather in the filament 123 may be emitted inside the pipe body 121, and the emitted electrons may be moved in a direction of the anode 124 while being accelerated inside the pipe body 121. The filament 123 of the cathode 122 may be made of tungsten (W).

In accordance with an exemplary embodiment, the anode 124 may be fixed as shown in FIG. 3. The fixed anode 124 may be cut at a predetermined angle, and a target 125 which collides with the electrons emitted and accelerated from the filament 123 may be formed in the cut portion.

The target 125 may be made of a metal such as tungsten (W), chrome (Cr), iron (Fe), nickel (Ni), or the like. In the target 125, a focus that is a collision surface with which the accelerated electrons collide may be formed in the target 125. Predetermined X-rays may be emitted in accordance with the collision of the accelerated electrons in the focus. The electrons emitted from the filament 123 of the cathode 122 may be rapidly decelerated by Coulomb force while colliding with the target 125. In this instance, in the target 125 formed in the anode 124, X-rays of energy corresponding to the applied tube voltage may be generated.

Although not shown, in accordance with another exemplary embodiment, the anode may have a rotatable disc-shape. In this case, the anode may be rotated about the axis through a direction in which the accelerated electrons are moved, at a predetermined rotation rate.

A boundary surface of the disc of the anode may be cut at a predetermined angle. In the cut portion of the boundary surface of the disc, a target with which the electrons emitted from the filament 123 collide may be formed in the same manner as above.

The X-rays generated in the anode 124 may be irradiated in a direction of the object (ob). In this case, on the irradiation path of the X-rays, a collimator 127 that can adjust an irradiation range or direction of the X-rays may be formed. The collimator 127 may pass the X-rays advancing in a specific direction, and absorb or reflect the X-rays advancing in a direction other than the specific direction to filter the X-rays. The collimator 127 may be made of a material that can absorb X-rays such as lead (Pb).

In accordance with an exemplary embodiment, the X-rays passing through the collimator 127 may be transmitted through a predetermined filter that can attenuate X-rays to a certain degree. The predetermined filter may be made of copper (Cu) or aluminum (Al).

The power source 126 may adjust X-ray energy generated in the anode 124 by applying a predetermined tube voltage and tube current to the anode 124 and the cathode 122 of the X-ray tube (t).

The energy or strength of the X-rays generated in the X-ray radiation unit 120 may be controlled in accordance with the tube voltage or tube current applied to the X-ray tube (t) or an X-ray exposure time.

The X-ray detection unit 130 may receive X-rays which have been irradiated in the X-ray radiation unit 120 and then transmitted through the object (ob) or X-rays which have been directly transmitted without reaching the object (ob), and then convert the received X-rays into predetermined electrical signals, that is, X-ray signals.

Figure 8:
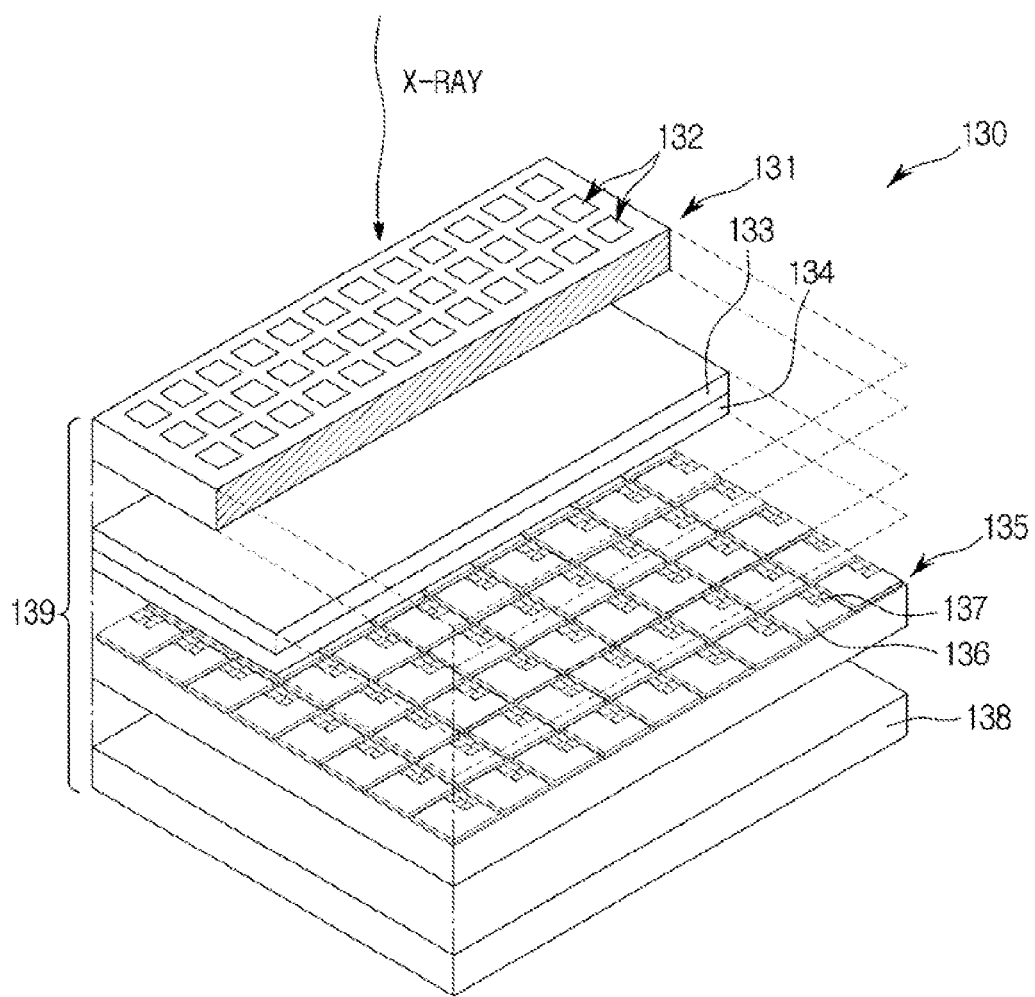
FIG. 8 is a perspective view illustrating an X-ray detection unit in accordance with an exemplary embodiment.

FIG. 8 is a perspective view illustrating an X-ray detection unit in accordance with an exemplary embodiment.

As shown in FIG. 8, the X-ray detection unit 130 may include a collimator 131 and an X-ray detection panel 139. A predetermined substrate 138 may be formed on a rear surface of the X-ray detection panel 139.

The collimator 131 of the X-ray detection unit 130 may filter scattered or refracted X-rays among the X-rays transmitted through the object (ob), so that the X-rays transmitted through the object (ob) may reach an appropriate pixel of the X-ray detection panel 139. The collimator 131 may include a plurality of partitions 132 made of lead (pb) or the like which can absorb the X-rays. The plurality of partitions may absorb the scattered or refracted X-rays so as to prevent the scattered or refracted X-rays from reaching the X-ray detection panel 139. Thus, the collimator 131 may absorb the X-rays scattered in the object (ob) to enable the X-rays suitable for image generation to reach the X-ray detection unit 130, thereby improving accuracy of the image.

The X-ray detection panel 139 may include a first electrode 133, a flat plate 135 in which a plurality of second electrodes (pixel electrodes) 136 are disposed, and a semiconductor material layer 134 disposed between the first electrode 133 and the flat plate 135.

The first electrode 133 may have a positive (+) or negative (−) polarity. Meanwhile, opposite to the first electrode 133, the second electrode 136 may have a negative (−) or positive (+) polarity. A predetermined bias voltage may be applied between the first electrode 133 and at least one of the second electrodes 136.

A charge-hole pair may be created in accordance with the incidence and absorption of the X-rays in the semiconductor material layer 134. The created charge-hole pair may be moved to the at least one second electrode 136 depending on the polarities of the first electrode 133 and the second electrode 136. In accordance with an exemplary embodiment, the semiconductor material layer 134 may be a photo conductor, and specifically, may be amorphous selenium.

The flat plate 135 may include the plurality of second electrodes 136 to which the created charge or hole is transmitted and a plurality of thin film transistors 137. In accordance with an exemplary embodiment, the flat plate 135 may include a plurality of CMOS chips. On each of the CMOS chips, a single second electrode 136 and a single thin film transistor 137 may be provided. The second electrode 136 may receive the hole or a negative charge transmitted from the semiconductor material layer 134. The hole or negative charge transmitted to the second electrode 136 may be stored in a predetermined storage device, for example, a capacitor. The thin film transistor 137 may read electrical signals which are transmitted from the second electrode 136 or stored in a predetermined storage device. As shown in FIG. 8, at least one thin film transistor 137 corresponding to each of the second electrodes 136 may be connected to each of the second electrodes 136. Thus, the X-ray detection unit 130 may convert the received X-rays into X-ray signals.

In the substrate 138 attached to the rear surface of the X-ray detection panel 139, various processors for controlling operations of the X-ray detection panel 139 may be installed. The processor or processors installed on the substrate 138 may control to read the electrical signals stored in the capacitor or the like. In addition, the substrate 138 may stably fix the X-ray detection panel 139.

Although not shown, in accordance with another exemplary embodiment, a phosphor screen may be disposed between the collimator 131 and the X-ray detection panel 139. The phosphor screen may receive the X-rays irradiated from the X-ray radiation unit 120 and emit predetermined light. In this case, on the above-described flat plate 135, at least one photo diode may be installed to receive the light output from the phosphor screen and convert the received light into electrical signals. The converted electrical signals may be stored in a storage device such as a capacitor.

In addition, although not shown, in accordance with still another exemplary embodiment, the X-ray detection panel may include a scintillator that can output a visible photon in accordance with the received X-rays and a photo diode that can detect the visible photon and be installed on the flat plate 135. The photo diode may output predetermined electrical signals in accordance with the visible photon, and the output electrical signals may be stored in the storage device such as a capacitor.

In accordance with an exemplary embodiment, the X-ray detection unit 130 may be a photon counting detector (PCD). The PCD may count photons greater than or equal to threshold energy from the X-ray signals, thereby acquiring predetermined data required for imaging an X-ray image.

The X-ray signals acquired by the X-ray detection unit 130 may be transmitted to the storage unit 140 or the image processing unit 150.

The storage unit 140 may temporarily or non-temporarily store the X-ray signals.

The image processing unit 150 may receive the X-ray signals from the X-ray detection unit 130 or the storage unit 140, and generate at least one X-ray image using the received X-ray signals. The image processing unit 150 may be controlled by the above-described control unit 110.

The image processing unit 150 may acquire a projection image with respect to the entire object (ob) or the FOV inside the object (ob) using the X-ray signals. When the projection image is acquired, the image processing unit 150 may calculate a DBP result value using the DBP method on the projection image. In this case, Equation 1 may be used.

The image processing unit 150 may reconstruct an image inside of the object by calculating an internal luminance value of the object (ob) using the calculated DBP result value. The image processing unit 150 may reconstruct only an image of the FOV inside the object.

In accordance with an exemplary embodiment, the image processing unit 150 may acquire the internal luminance value of the FOV inside the object (ob) by calculating a value for satisfying at least one condition or a value for minimizing or maximizing at least one cost function, and reconstruct an image of the FOV inside the object (ob) using the acquired internal luminance value. In this case, the image processing unit 150 may reconstruct the image of the FOV of the object (ob) using a POCS method or PPXA.

The image processing unit 150 may reconstruct the image of the FOV inside the object (ob) using a regulation function such as total variation (TV). The regulation function may be selected by a user through the input unit 20 or the like, or determined in accordance with a setting of the system. In addition, the image processing unit 150 may reconstruct the image of the FOV inside the object (ob) further using information about the outline of the object (ob).

In accordance with an exemplary embodiment, the image processing unit 150 may acquire the internal luminance value of the FOV inside the object (ob) by detecting a value for satisfying the above-described first to fifth conditions. In this case, an iterative reconstruction method may be used. Specifically, Equations 5 to 9 may be used in order to mathematically calculate the first to fifth conditions.

In accordance with another exemplary embodiment, the image processing unit 150 may acquire at least one optimal internal luminance value by detecting a value for minimizing a sum (Equation 10) of the above-described first to fourth cost functions. The first to fourth cost functions may be represented as Equations 11 to 14. Here, the fourth cost function may be a regulation function, for example, total variation with respect to the internal luminance value. However, the regulation function that can be used in the fourth cost function is not limited to the total variation (TV), and other regulation functions may be also used.

The image post-processing unit 160 may further perform post-processing with respect to the X-ray image reconstructed in the image processing unit 150. For example, the image post-processing unit 160 may correct brightness or luminance of the whole or a part of the X-ray image, contrast, sharpness, and the like by a user. The image post-processing unit 160 may correct the X-ray image in accordance with an instruction or a command of the user or setting defined in advance.

The display unit 2 may display, to the user, the image reconstructed in the image processing unit 150 or the image on which additional post-processing is performed in the image post-processing unit 160. The display unit 2 may be a display device installed in the X-ray imaging apparatus 98, or a display device such as a monitor device installed in or connected to a separate external workstation.

Figure 9:
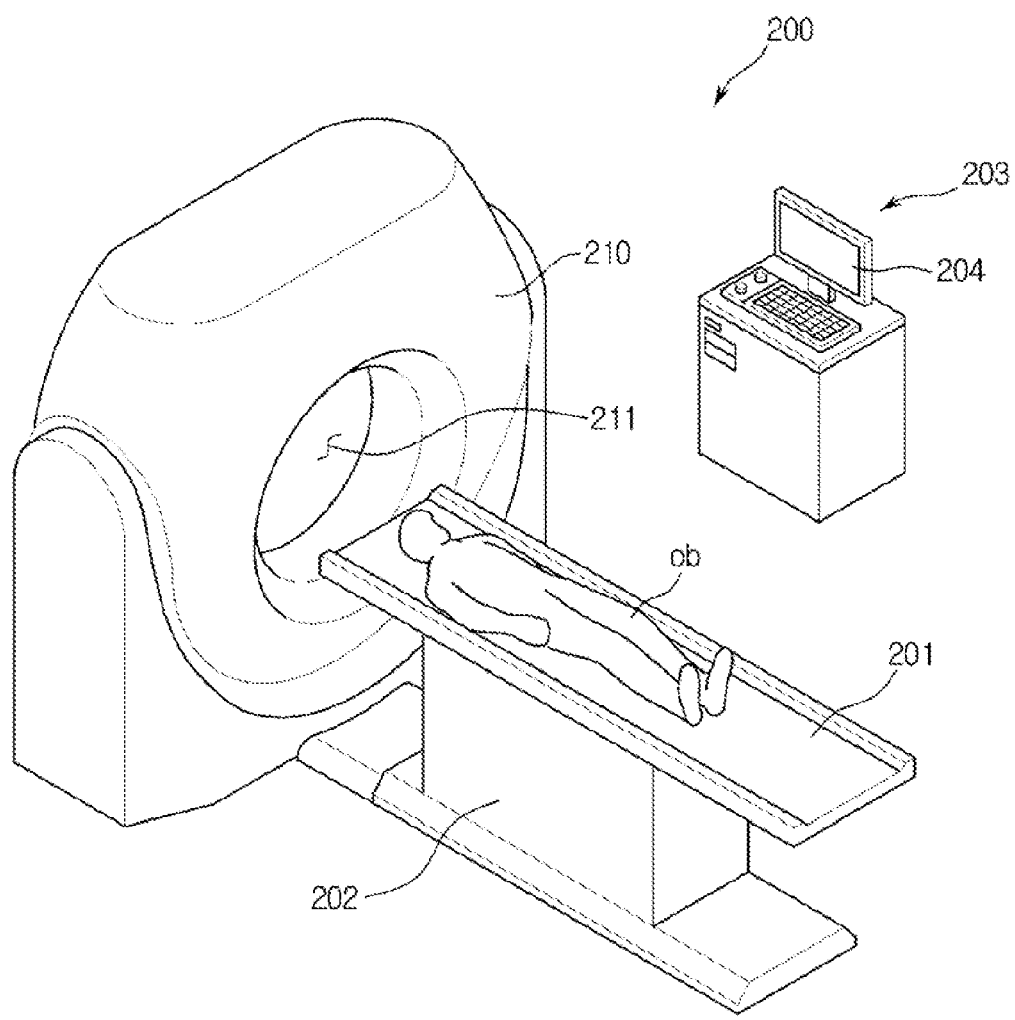
FIG. 9 is a perspective view illustrating a computed tomography (CT) imaging apparatus in accordance with an exemplary embodiment.
Figure 10:
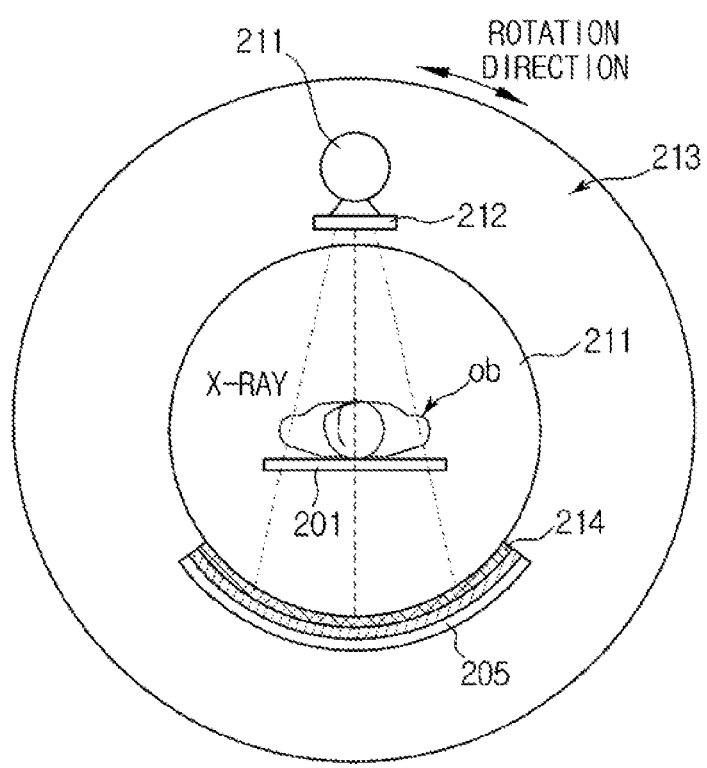
FIG. 10 illustrates a CT imaging apparatus in accordance with an exemplary embodiment.
Figure 11:
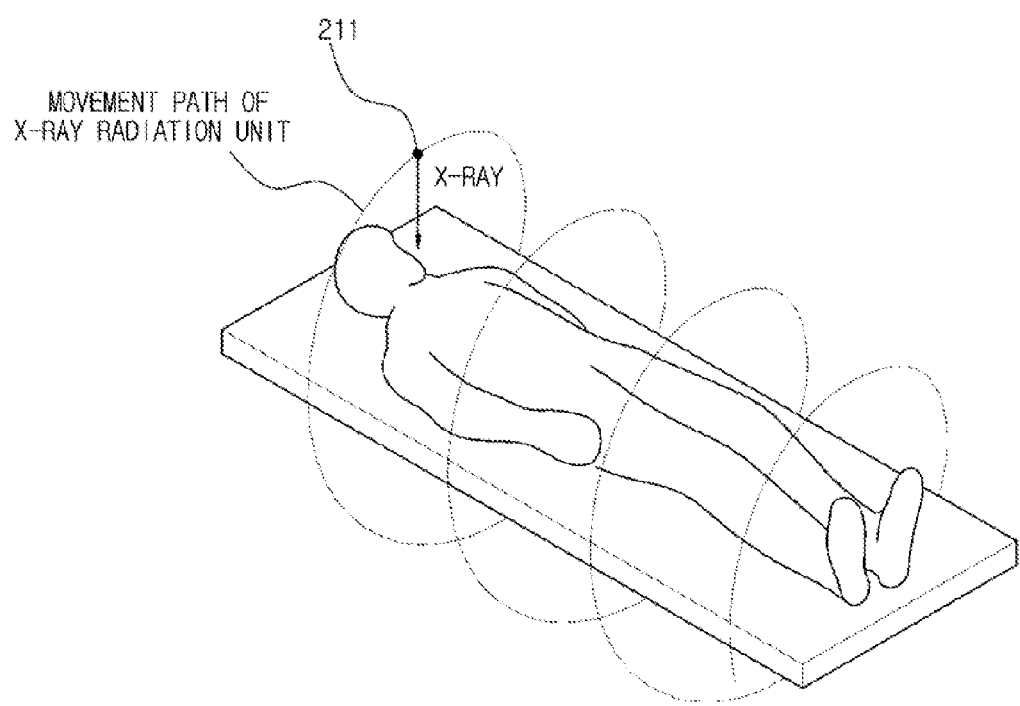
FIG. 11 illustrates X-ray irradiation of a CT imaging apparatus.

FIG. 9 is a perspective view illustrating a computed tomography (CT) imaging apparatus in accordance with an exemplary embodiment, FIG. 10 illustrates a CT imaging apparatus in accordance with an exemplary embodiment, and FIG. 11 illustrates X-ray irradiation of a CT imaging apparatus.

Hereinafter, as an example of the X-ray imaging apparatus 98, a CT imaging apparatus 200 will be described.

As shown in FIG. 9, the CT imaging apparatus 200 may include a housing 210 in which a bore 211 is formed near the center thereof, a holding unit 201 (e.g., holder) in which the object (ob) is placed, and a support 202 that supports the holding unit 201. The holding unit 201, on which the object (ob) is placed on an upper portion thereof, may be transported inside of the bore 211 of the housing 210 and a gantry 213 at a predetermined speed in accordance with operations of a driving unit such as a separate motor or the like. In this instance, the object (ob) placed on the upper portion of the holding unit 201 may be transported together with the holding unit 201 to the inside of the bore 211.

In accordance with an exemplary embodiment, the CT imaging apparatus 200 may be connected to an information processing apparatus 204 that displays an image of the object (ob) or receives various control commands for the CT imaging apparatus 200 from a user, through a wired/wireless communication network. The information processing apparatus 204 may include a display unit 203 for displaying X-ray images to a user, and include a processor for controlling the CT imaging apparatus 200, as necessary.

The gantry 213 that is rotatable about a predetermined shaft may be installed inside the housing 210, and an X-ray irradiation unit 212 and an X-ray detection unit 214 may be installed in the gantry 213.

The gantry 213 may be rotated at a predetermined angular velocity by a gantry driving unit driven in accordance with control commands of the processor. Thus, the X-ray irradiation unit 212 and the X-ray detection unit 214 which are installed in the gantry 213 may also be rotated about the predetermined shaft. A rotation direction of the gantry is not limited as shown in FIG. 10.

The X-ray irradiation unit 212 and the X-ray detection unit 214 may be installed in positions facing each other. Thus, the X-rays irradiated from the X-ray irradiation unit 212 may be detected by the X-ray detection unit 214. The X-ray irradiation unit 212 and the X-ray detection unit 214 may be substantially the same as the structure or principle of the X-ray radiation unit 120 and the X-ray detection unit 130 which has been described with reference to FIGS. 6 to 8.

When CT imaging is started, the holding unit 201 may transport the object (ob) to the inside of the bore 211, and the gantry 213 may start to be rotated in accordance with a rotation rate and a rotation speed which are input from a user or stored in advance. In addition, the X-ray irradiation unit 212 irradiates the object (ob) transported to the inside of the bore 211 with X-rays of a predetermined energy spectrum. In this case, the X-ray irradiation unit 212 and the X-ray detection unit 214 may be rotated around the object (ob) in accordance with the rotation of the gantry 213. The X-ray detection unit 214 may detect the X-rays transmitted through the object (ob) while being rotated together with the X-ray irradiation unit 212, and convert the detected X-rays into electrical signals.

Since the holding unit 201 transports the object (ob) to the inside of the housing 210 while the X-ray irradiation unit 212 irradiates the object (ob) with X-rays while being rotated, the X-ray irradiation unit 212 irradiates the object (ob) with the X-rays while moving along a helical movement path as shown in FIG. 11 in terms of the object (ob). The X-ray detection unit 214 may be also moved along the helical movement path in a symmetrical manner to the X-ray irradiation unit 212 on the basis of the object (ob).

Thus, the X-ray irradiation unit may irradiate the object (ob) with the X-rays while moving around the object (ob) along the helical trajectory, thereby acquiring the X-ray signals. In this case, the X-ray irradiation unit 212 may irradiate only the FOV inside the object (ob) with the X-rays as shown in FIG. 3. As shown in FIG. 3, the FOV may include a cylindrical shape.

In this case, the processor installed in the CT imaging apparatus or a separate workstation may reconstruct a three-dimensional image using a set of PI lines in the same manner as described above with respect to FIG. 2A and FIG. 2B.

More specifically, the processor of the CT imaging apparatus may acquire a projection image from the projection image acquired by the X-ray detection unit 214, and acquire a DBP result value by performing a DBP method with respect to the projection image. Next, the processor may reconstruct an image using a relationship between the DBP result value and the internal luminance value. In this case, the DBP result value and the internal luminance value may have a Hilbert-transforming relationship. The processor may acquire at least one optimal internal luminance value using the POCS method or PPXA when reconstructing the image. In this case, the above-described first to fifth conditions (Equations 5 to 9) may be used, and the first to fourth cost functions (Equations 11 to 14) may be used. When using the cost function, a value for minimizing a sum (Equation 10) of the first to fourth cost functions may be detected to acquire the optimal internal luminance value.

Hereinafter, a method of reconstructing an X-ray image will be described with reference to FIG. 12.

Figure 12:
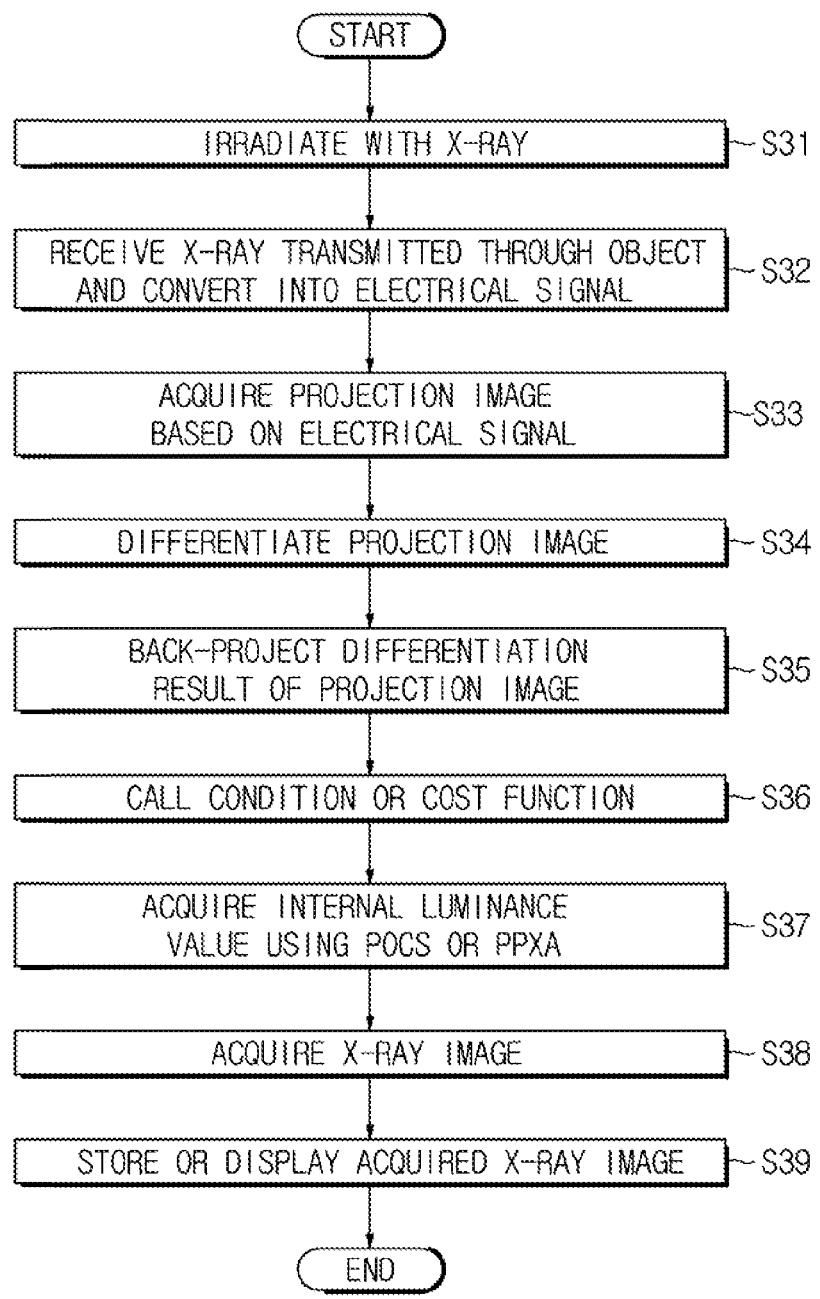
FIG. 12 is a flowchart illustrating a method of reconstructing an X-ray image.

FIG. 12 is a flowchart illustrating a method of reconstructing an X-ray image.

As shown in FIG. 12, in operation S31, X-rays of a predetermined energy spectrum may be irradiated on an object. In this case, the X-ray irradiation unit that irradiates the object with the X-rays may be fixed or movable. When the X-ray irradiation unit is movable, the X-ray irradiation unit may be rotationally moved with respect to the object.

The X-rays may reach the object, be attenuated in accordance with an attenuation rate of internal materials of the object, and then be transmitted. In some cases, the X-rays may not be transmitted through the object because they are all attenuated by the internal materials of the object. In operation S32, the X-ray detection unit may detect the X-rays transmitted through the object, and convert the detected X-rays into electrical signals, that is, X-ray signals, to output the converted signals.

In operation S33, when the X-ray signals are output, a projection image corresponding to the X-ray signals may be acquired based on the X-ray signals.

Next, in operation S34, a differentiation result of the projection image may be acquired by differentiating the acquired projection image. Next, in operation S35, a DBP result value may be acquired by back-projecting the differentiation result of the projection image.

Next, in accordance with an exemplary embodiment, predetermined conditions, for example, the first to fifth conditions may be called and loaded in a storage space such as a RAM or buffer. In accordance with another exemplary embodiment, predetermined cost functions, for example, the first to fourth cost functions may be called in operation S36.

When the predetermined condition or cost function is called and loaded in the RAM or the like, at least one optimal internal luminance value may be acquired using the POCS method or PPXA. In this case, when the predetermined condition is called, the POCS method may be used, and when the predetermined cost function is called, the PPXA may be used in operation S37.

When the at least one optimal internal luminance value is acquired, an X-ray image may be generated based on the acquired internal luminance value in operation S38.

The acquired X-ray image may be stored in a storage device such as a magnetic disk storage device or a semiconductor storage device. In addition, the acquired X-ray image may be displayed to a user through a display device.

According to the above-described image reconstruction unit, X-ray imaging apparatus, and method of reconstructing the image, a time required for reconstructing the image based on the collected signals may be shortened.

In addition, according to the above-described image reconstruction unit, X-ray imaging apparatus, and method of reconstructing the image, an accurate image may be reconstructed even though some information about the inside of the object cannot be understood.

Moreover, according to the above-described X-ray imaging apparatus and the method of reconstructing the image, when an X-ray image of the FOV of the object is acquired by irradiating the FOV of the object with X-rays, the X-ray image of the FOV of the object may be rapidly and accurately reconstructed even though some of information about the inside of the object cannot be understood.

Since the X-ray image may be rapidly and accurately acquired by irradiating the FOV of the object with X-rays, an exposure rate with respect to the object may be reduced by reducing an X-ray irradiation range with respect to the object.

In addition, the detector of the X-ray imaging apparatus may be miniaturized, and therefore the X-ray imaging apparatus may be miniaturized and an economical effect due to a cost reduction of the X-ray imaging apparatus may be obtained.

Furthermore, when the above-described image reconstruction unit and the method of reconstructing the image are applied to an interior tomography apparatus and method, problems of the interior tomography such as a long reconstruction time and having to know the internal luminance value of the object may be solved.

Although a few exemplary embodiments have been shown and described, it would be appreciated by those skilled in the art that changes may be made in these exemplary embodiments without departing from the principles and spirit of the invention, the scope of which is defined in the claims and their equivalents.

What is claimed is:

1. A method of reconstructing an image, comprising:
   calculating a derivative back projection (DBP) result value using a DBP method with respect to a projection image of a field of view (FOV) inside an object; and
   reconstructing an image of the FOV by using the DBP result value, and further using a regulation function which defines an internal luminance value of the FOV inside the object.

2. The method according to claim 1, wherein the regulation function is a regulation function acquired using total variation (TV).

3. The method according to claim 2, wherein the regulation function acquired using TV is calculated using an internal luminance value inside the object.

4. The method according to claim 1, wherein the reconstructing the image includes:
   reconstructing the image of the FOV using a relationship between a conversion value acquired by performing a Hilbert transform on the internal luminance value of the FOV and the calculated DBP result value.

5. The method according to claim 1, wherein the reconstructing the image includes:
   reconstructing the image using an iterative reconstruction method.

6. The method according to claim 1, wherein the reconstructing the image includes:
   reconstructing the image of the FOV using the internal luminance value of the FOV or a cost function with respect to the internal luminance value of the FOV.

7. The method according to claim 6, wherein the cost function is acquired by the regulation function.

8. The method according to claim 7, wherein the regulation function is a regulation function acquired using total variation (TV).

9. The method according to claim 1, wherein the reconstructing the image includes:
   reconstructing the image of the FOV using a projection onto a convex set (POCS) method or a parallel proximal algorithm (PPXA).

10. The method according to claim 1, further comprising:
    acquiring the projection image of the FOV by irradiating the FOV with X-rays and receiving the X-rays having passed through the FOV.

11. An X-ray imaging apparatus comprising:
    an X-ray radiator configured to irradiate a field of view (FOV) inside an object with X-rays;
    an X-ray detector configured to output electrical signals by converting the X-rays having passed through the FOV; and
    an image processor configured to acquire a projection image of the FOV inside the object based on the electrical signals, calculate a derivative back projection (DBP) result value using a DBP method with respect to the projection image, and reconstruct an image of the FOV by using the DBP result value and a regulation function which defines an internal luminance value of the FOV inside the object.

12. The X-ray imaging apparatus according to claim 11, wherein at least one of the X-ray radiator and the X-ray detector are configured to rotate around the object.

13. The X-ray imaging apparatus according to claim 11, wherein the image processor is further configured to acquire the regulation function by using total variation (TV).

14. The image reconstruction unit according to claim 13, wherein the regulation function acquired using TV is calculated using an internal luminance value inside the object.

15. The X-ray imaging apparatus according to claim 11, wherein the image processor is further configured to reconstruct the image of the FOV using a relationship between a conversion value acquired by performing a Hilbert transform on the internal luminance value of the FOV and the calculated DBP result value.

16. The X-ray imaging apparatus according to claim 11, wherein the image processor is further configured to reconstruct the image using an iterative reconstruction method.

17. The X-ray imaging apparatus according to claim 11, wherein the image processor is further configured to reconstruct the image of the FOV using the internal luminance value of the FOV or a cost function with respect to the internal luminance value of the FOV.

18. The X-ray imaging apparatus according to claim 17, wherein the image processor is further configured to acquire the cost function by using the regulation function.

19. The X-ray imaging apparatus according to claim 11, wherein the image processor is further configured to reconstruct the image of the FOV using a projection onto a convex set (POCS) method or a parallel proximal algorithm (PPXA).

\* \* \* \* \*